US00PP27749P3

(12) United States Plant Patent
Bak et al.

(10) Patent No.: US PP27,749 P3
(45) Date of Patent: Mar. 7, 2017

(54) ***MEDINILLA* HYBRID PLANT NAMED 'AROSA'**

(50) Latin Name: ***Medinilla* hybrid**
Varietal Denomination: Arosa

(71) Applicants: Elly Bak, Rijsenhout (NL); Nicolaas Steur, Oude Niedorp (NL)

(72) Inventors: Elly Bak, Rijsenhout (NL); Nicolaas Steur, Oude Niedorp (NL)

(73) Assignee: Corn Bak B.V. (NL)

( * ) Notice: Subject to any disclaimer, the term of this patent is extended or adjusted under 35 U.S.C. 154(b) by 174 days.

(21) Appl. No.: 14/121,492

(22) Filed: Sep. 10, 2014

(65) Prior Publication Data

US 2016/0073564 P1 Mar. 10, 2016

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Keith Robinson
(74) *Attorney, Agent, or Firm* — Cassandra Bright

(57) ABSTRACT

A new and distinct *Medinilla* hybrid plant named 'AROSA', characterized by an erect shrub plant, measuring about 30 cm in total height (when first flowering) and about 40 cm in diameter; green colored leaves, measuring about 13-18 cm in length and bout 7 cm in width; pendulous panicle, measuring about 20 cm in length and about 10 cm in diameter, with red-purple (RHS 65D) flowers.

1 Drawing Sheet

Latin name of the genus and species: *Medinilla* hybrid.
Variety denomination: 'AROSA'.

BACKGROUND OF THE INVENTION

The present invention relates to a new and distinct hybrid cultivar of *Medinilla* plant, botanically known as *Medinilla* hybrid, hereinafter referred to by the cultivar name 'AROSA'. The genus of *Medinilla* belongs to the Melastomataceae family.

The new *Medinilla* 'AROSA' is a product of a planned breeding program conducted by the inventors, Elly Bak and Nico D. M. Steur, in Assendelft, The Netherlands. The objective of the breeding program is to develop a new *Medinilla* variety with a good growing habit and attractive inflorescence.

The new *Medinilla* 'AROSA' is the result of some generations of selection in a *Medinilla* hybrid. The female or seed parent of the hybrid is proprietary, unpatented *Medinilla* selection identified by code 82984514. The male or pollen parent of the hybrid is proprietary, unpatented *Medinilla* selection identified by code 82981030. The crossing resulting in *Medinilla* 'AROSA' was made during 2009 and with the plant flowered for the first time in 2011 in Assendelft, the Netherlands.

Asexual reproduction of the new *Medinilla* hybrid 'AROSA' performed by vegetative means by cuttings was first performed in 2011, in Assendelft, the Netherlands. The first 'AROSA' plants propagated through the use of cuttings flowered in 2012 in Assendelft, the Netherlands, and have demonstrated that the combination of characteristics herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be unique characteristics of 'AROSA' which in combination distinguish the *Medinilla* hybrid as a new and distinct cultivar:

1. Solid growth habit;
2. Erect shrub plant, measuring about 30 cm in height (above the pot when first flowering);
3. Green colored leaves, measuring about 13-18 cm in length and about 7 cm in width;
4. Pendulous panicles with red-purple (RHS 65D) colored flowers.

Of the many commercials cultivars known to the present inventors, the most similar in comparison to the new *Medinilla* 'AROSA' is the *Medinilla* 'MAGIC' U.S. Plant Pat. No. 25,349. Plants of the new *Medinilla* 'AROSA' differ from plants of the *Medinilla* 'MAGIC' primarily in leaf size. Plants of 'MAGIC' have smaller leaves than plants of 'AROSA'.

BRIEF DESCRIPTION OF THE PHOTOGRAPHS

The accompanying photograph illustrates the overall appearance of the new *Medinilla* 'AROSA' showing the colors as true as is reasonably possible with colored reproductions of this type. Colors in the photograph may differ slightly from the color values cited in the detailed botanical description which accurately describes the color of 'AROSA'.

FIG. 1 shows a side view perspective of a typical potted flowering plant of 'AROSA' at about 50 weeks from potting.

DETAILED BOTANICAL DESCRIPTION

'AROSA' has not been observed under all possible environmental conditions. The phenotype of the new cultivar may vary with the variations in environment such as temperature, light intensity, day length, fertilizers and humidity without any change in the genotype of the plant.

The aforementioned photograph, together with the following observations, measurements and values describes the new *Medinilla* 'AROSA' as grown in a greenhouse in Assendelft, the Netherlands, under conditions which closely approximate those generally used in commercial practice.

Color references are made to The Royal Horticultural Society Colour Chart (R.H.S.), 2001 Edition, except where general colors of ordinary significance are used. Color values were taken under daylight conditions in a greenhouse in Assendelft, the Netherlands. The age of the plants of 'AROSA' described is about 50 weeks from potting.

Botanical: *Medinilla* hybrid.

Propagation: Vegetative cuttings.

*Time to initiate roots*.—Summer: 21 to 28 days at approximately 20-23° C. Winter: 28 to 35 days at approximately 20-23° C.

*Time to a rooted young plant*.—Approximately 4 weeks.

Root description: Moderately dense, non-fleshy, non-fibrous, moderately thick, colored Near Greyed-Orange RHS N170A to N170B.

Plant:

*General appearance and form*.—Height: About 30 cm. Diameter: About 40 cm. Shape: Semi-upright fleshy plant with pendulous flowers.

*Growth habit*.—Semi-upright.

*Plant vigor*.—Moderate to vigorous.

*Flowering season*.—From April till October.

*Cold tolerance*.—Frost tender, temperatures below 5 degree C. may damage plants.

*Fragrance*.—None.

*Primary lateral branches*.—Quantity: 3 to 7. Shape: Square and winged. Wings approximately 2 mm wide and 8 mm long. Internode length: Average range around 4 to 7 cm. Color: Near RHS 143A. Length: Approximately 15 to 25 cm. Width: 1.0 to 1.5 cm. Texture: Glabrous.

Foliage:

*Quantity*.—About 30.

*Arrangement*.—Opposite.

*Size*.—Length: About 13 to 18 cm. Width: About 7 cm.

*Overall shape*.—Broadly ovate.

*Apex shape*.—Cuspidate.

*Base shape*.—Acute.

*Margin*.—Entire, slightly undulate.

*Texture*.—Glabrous, upper and lower surfaces.

*Color*.—Leaf color can vary somewhat depending on growing conditions. Upper surface: Glossy green, closest to RHS 139A. Lower surface: Glossy, closest to RHS 137C.

*Venation*.—Parallel, sunken, the venation is slightly below the surface of the rest of the leaf. Upper surface: Near RHS Yellow-Green 144B. Lower surface: Near RHS Yellow-Green 146B.

*Petiole*.—Not present, leaves sessile.

*Stipule description*.—No stipules present.

Inflorescence:

*Natural flowering season*.—Spring to early Summer in tropical conditions. Commercial plants are induced to flower with cold treat, which can be used year-round.

*Typical commercial flowering technique and time*.—To induce flowering, maintain the plant at 18 degrees Celsius for about ten weeks. Year around flowering occurs under the condition that plants receive this cold treatment.

*Days to flowering from rooted cutting*.—Approximately 50 weeks.

*Persistent or self-cleaning*.—Self-cleaning.

*Shape*.—Pendulous panicles.

*Amount*.—About 10 per plant (depending on the size of the plant).

*Size*.—Length: About 20 cm. Width: About 10 cm.

*Corolla*.—Number: about 190 per panicle. Length: About 20 mm. Width: About 10 mm.

*Petals*.—Number: 4 or 5 per flower. Length: 14 mm. Width: 8 mm. Overall Shape: obovate, asymmetrical. Arrangement: Rotate. Base: Cuneate. Margin: Entire. Texture: Glabrous all surfaces. Apex Shape: obtuse. Color: Upper surface and lower: while, closest to RHS 155B.

*Sepals*.—Fused together, enclosing the ovary. Less than 8 mm. Color: red-purple, closest to RHS 65D. Quantity: Single structure identifiable, round in shape, no individual apex. Length: Maximum 8 mm. Width: Approximately 4 mm. Base: Fused. Margin: entirely fused. Texture: Glabrous all surfaces.

*Bracts*.—Quantity: 2 per crown. Arrangement: Verticillate. Size: Length: about 1-18 mm. Width: less than 1-13 mm. Overall shape: ovate. Color: Near RHS Red-Purple 64B and Yellow-Green 144B. Apex: Acute. Base: Truncate. Margin: Entire. Texture: Glabrous all surfaces.

*Bud*.—Size: Length: about 12 mm. Width: about 4 mm. Shape: Ovate. Texture: Glabrous. Color: Near RHS Red-Purple 62D.

*Peduncle*.—Length: About 7.0 cm. Diameter: About 0.3 cm. Color: RHS Yellow-Green 144B, over time changing to Red-Purple 64A. Texture: glabrous. Strength: Very strong.

*Pedicel*.—Length: Average range approximately 0.5 cm to 20 cm. Shorter pedicels occurring with terminal flowers, longer towards base of inflorescence. Diameter: About 0.10 cm. Texture: Glabrous. Strength: Strong. Color: RHS Red-Purple 65A.

Reproductive organs:

*Androecium*.—Stamen: Number: 8 per flower. Length: 10 mm. Diameter: 1 mm. Color: yellow, with a white base (too small to qualify RHS value). Anther: Length: 8 mm. Width: 2 mm. Shape: Basifixed, linear. Color: Violet, closest to RHS 86B, with a yellow base (base too small to qualify RHS value). Pollen: not visible.

*Gynoecium*.—Pistil: Number: 1 per flower. Length: 19 mm. Stigma: Width: less than 1 mm. Color: white, too small to qualify RHS value. Shape: acute. Style: Length: 16 mm. Color: white, closest to RHS 155B. Ovary: Shape: round. Position: inferior. Length: 3 mm. Diameter: 3 mm. Color: white, closest to RHS 155C.

Seeds:

*Amount*.—Approximately 50 to 200 per fruit.

*Shape*.—Obovate glabrous.

*Size*.—Less than 1 mm in diameter.

*Color at maturity*.—Grey-orange, closest to RHS 165B.

Fruit:

*Type*.—Berry.

*Shape*.—Round.

*Texture*.—Smooth.

*Size*.—0.5-1 cm in diameter.

*Color at maturity*.—Grey purple closest to 187A.

Disease/pest resistance: Neither resistance nor susceptibility to the normal diseases and pests of *Medinilla* have been observed.

What is claimed is:

1. A new and distinct *Medinilla* plant named 'AROSA', as illustrated and described herein.

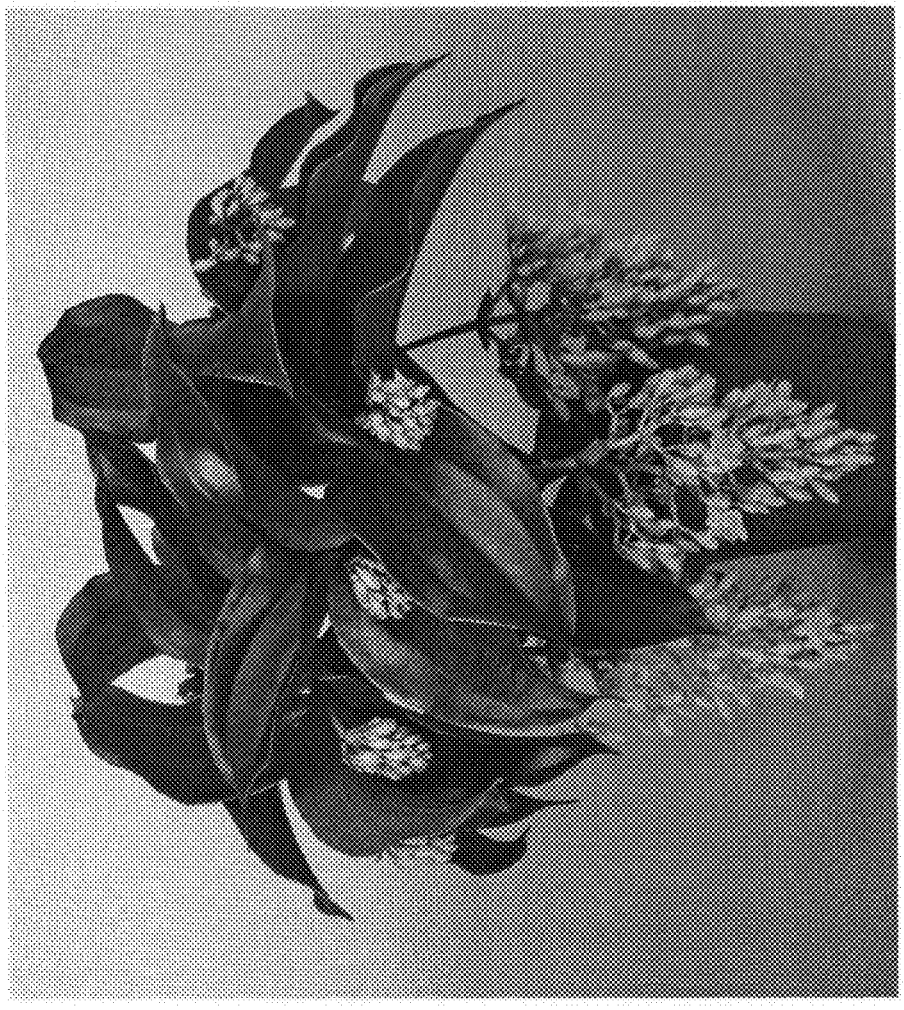

* * * * *